United States Patent [19]

O'Neill et al.

[11] 3,954,893

[45] May 4, 1976

[54] HALOGENATED CYCLOBUTANES

[75] Inventors: Gerald J. O'Neill; Robert S. Holdsworth, both of Arlington; Charles W. Simons, Bedford, all of Mass.

[73] Assignee: W. R. Grace & Co., Cambridge, Mass.

[22] Filed: Jan. 10, 1975

[21] Appl. No.: 539,957

Related U.S. Application Data

[63] Continuation-in-part of Ser. No. 394,975, Sept. 7, 1973, Pat. No. 3,870,797, which is a continuation of Ser. Nos. 170,280, Aug. 9, 1971, abandoned, and Ser. No. 170,331, Aug. 9, 1971, abandoned, and Ser. No. 170,293, Aug. 9, 1971, abandoned, said Ser. No. 170,280, is a continuation-in-part of Ser. No. 91,521, Nov. 20, 1970, abandoned, said Ser. No. 170,331, is a continuation-in-part of Ser. No. 93,437, Nov. 27, 1970, abandoned, and Ser. No. 141,934, May 10, 1971, abandoned.

[52] U.S. Cl. .............................. 260/648 F; 424/352
[51] Int. Cl.² ....................................... C07C 23/06
[58] Field of Search .................. 260/648 F; 424/352

[56] References Cited
UNITED STATES PATENTS 2,462,345  2/1949  Barrick............................ 260/648 F
2,480,560  8/1949  Downing et al. ................ 260/648 F

OTHER PUBLICATIONS

Park et al., Chem. Abstracts 54, 19521$^i$(1960).
Park et al. (I), Chem. Abs. 71 90710z (1969).
Holdsworth et al., Chem. Abs. 74884c and 74885d, Vol. 77 (1972).
Holdsworth et al. (I), Chem. Abs. 78 124135$^r$ (1973).

*Primary Examiner*—D. Horwitz
*Attorney, Agent, or Firm*—Armand McMillan; C. Edward Parker

[57] ABSTRACT

Certain new halogenated cyclobutanes have been synthesized and found to possess utility as inhalation anesthetics. They are: 1,4-dichloro-1,2,2-trifluorocyclobutane, 1-chloro-1,2,2,4-tetrafluorocyclobutane, 1,4-dichloro-1,2,2,4-tetrafluorocyclobutane, 1-chloro-1,2,2,3,3-pentafluorocyclobutane, 1,2,2-trifluorocyclobutane, 1-chloro-2,3,3-trifluorocyclobutane, 1-chloro-2,4 4-trifluorocyclobutane, 1-bromo-1,2,2-trifluorocyclobutane, 1-bromo-2-methyl-1,4,4-trifluorocyclobutane and 1-bromo-2-chloro-1,4,4-trifluorocyclobutane.

8 Claims, No Drawings

NEW HALOGENATED CYCLOBUTANES

CROSS-REFERENCE TO RELATED APPLICATIONS

This is a continuation-in-part of application Ser. No. 394,975 filed on Sept. 7, 1973 now Pat. No. 3,870,797. The latter application is a continuation of applications Ser. Nos. 170,280, 170,331 and 170,293 filed on Aug. 9, 1971. Application Ser. No. 170,280 is in turn a continuation-in-part of Ser. No. 91,521 filed on Nov. 20, 1970, while application Ser. No. 170,331 is a continuation-in-part of Ser. No. 93,437 filed on Nov. 27, 1970 and Ser. No. 141,934 filed May 10, 1971. All these applications, with the exception of Ser. No. 394,975 which supports use claims for the compounds of this invention, have been abandoned.

THE PRIOR ART

In the continuing search for safe, effective inhalation anesthetics that began with the introduction of chloroform in the middle of the last century, surprisingly few compounds have qualified for that drastic yet delicate role. This penury derives in part from the unpredictable chemical and physiological properties and behavior of plausible compounds such as for instance the lower halogenated alkanes, as well as from the lack of understanding of the mode of action of anesthetics in general. While some superficial parameters have been evolved to gauge a few of the necessary properties of a good inhalation anesthetic: e.g., a certain oil-water distribution coefficient and the negative influence of fluoride as opposed to that of chloride, the discovery of a useful anesthetic agent remains beyond the scope of the routine expertise of both the chemist and the physiologist.

Thus, it is, for instance, that while cyclopropane is recognized as an effective if inflammable anesthetic, one of its higher water-insoluble homologs, cyclopentane, has no medical use. As to cyclobutanes, a recent review of the state of the art [Larsen, E. R., Fluorine Chemistry Reviews, Vol. 3, pages 1 and 34 (1969)] is no more enlightening in its report that of three closely related fluorocyclobutanes, one is said to possess anesthetic properties (1,2-dihydrohexafluoro-) while the others are toxic (1,2-dichlorohexafluoro-) and inactive (octafluoro-) respectively.

With respect to the chemical nature of the halocyclopropanes herein disclosed, it is noted that they are new compounds and that, while similar compounds have been heretofore synthesized [Barrick, U.S. Pat. 2,462,345 and 2,462,347], no possibility of anesthetic power has been disclosed or suggested by anyone.

Burns et al, the original investigators of the cyclobutanes reviewed by Larsen, conclude that "It is suggested that none of the compounds is sufficiently promising to justify further investigation at this time." [Burns et al, Anesthesia 19 (2), 168 (1964)]. With respect to 1,2-dihydrohexafluorocyclobutane, the only anesthetic halocyclobutane of the art, the judgement just quoted has found ample support as demonstrated in Example XIV of the present specification. Kranz and Rudo, after an extensive review of the pharmacological properties of fluorine compounds, also conclude that "cyclic halogenated compounds tend to be toxic". [Handbuch Exp. Pharm. 20 (1), 541 (1966)].

SUMMARY OF THE INVENTION

Certain new 1-chloro-1,2,2-trifluorocyclobutanes have now been synthesized and found to possess inhalation anesthetic properties and not cause convulsions and death when administered in concentrations within the useful range. The compounds found to possess this utility are 1,4-dichloro-1,2,2-trifluorocyclobutane, 1-chloro-1,2,2,4-tetrafluorocyclobutane, 1,4-dichloro-1,2,2,4-tetrafluorocyclobutane, 1-chloro-1,2,2,3,3-pentafluorocyclobutane, 1,2,2-trifluorocyclobutane, 1-chloro-2,3,3-trifluorocyclobutane, 1-chloro-2,4,4-trifluorocyclobutane, 1-bromo-1,2,2-trifluorocyclobutane, 1-bromo-2-methyl-1,4,4-trifluorocyclobutane and 1-bromo-2-chloro-1,4,4-trifluorocyclobutane.

DETAILED DESCRIPTION

The compounds of this invention can be prepared by cyclizing appropriately selected ethylenic compounds in an autoclave according to the method of Coffman et al. [J. Am. Chem. Soc. 71, 490 (1949)]. The ethylenic compounds are typically charged into the autoclave and heated at a suitable temperature; e.g. at about 200°C, for a period of, for example, about 7 hours at autogenous pressure. When the reaction is complete, the autoclave is cooled and gaseous substances are evacuated through a cold trap. The liquid content is then removed and subjected to a preliminary distillation followed by final purification by means of preparatory scale vapor phase chromatography or by other suitable techniques. Compounds of sufficiently high purity for anesthetic use are obtained in this manner.

The ethylenic compounds employed in synthesizing the anesthetic products of this invention are listed in the Table 1 along with some of the physical properties of the products. In the case of new compounds, the cyclic structure as well as the number and type of ring substituents were confirmed by analysis of the NMR spectra.

TABLE I

Synthesis and Physical Properties of Anesthetic Compounds

| Ex. | Cyclobutane | Reactants | Density $(d_4')$ | Boiling Point |
|---|---|---|---|---|
| I | 1,4-dichloro-1,2,2,4-tetrafluoro- | ClFC=CF$_2$ + vinyl chloride | $1.5+^{20}$ $1.5+^{20}$ | (a) 104°C (b) 107°C |
| II | 1-chloro-1,2,2,4-tetrafluoro- | ClFC=CF$_2$ + vinyl fluoride | $1.467^{20}$ | 80°C |
| III | 1,4-dichloro-1,2,2,4-tetrafluoro- | ClFC=CF$_2$ + CFC=CH$_2$ | $1.547^{20}$ | 90.5°C |
| IV | 1-chloro-2,3,3-trifluoro- | CHF=CF$_2$ + vinyl chloride | $1.4+^{20}$ | 80–82°C |
| V | 1-chloro-1,2,2,3,3-pentafluoro- | CF$_2$=CF$_2$ + CFCl=CH$_2$ | $1.568^{20}$ | 55°C |
| VI | 1-chloro-2,4,4-trifluoro- | ClHC=CF$_2$ + vinyl fluoride | $1.4+^{20}$ | 80°C |
| VII | 1,2,2-trifluoro- | CF$_2$=CFCl + ethylene* | $1.198^{20}$ | 66.5°C |

TABLE I-continued

Synthesis and Physical Properties of Anesthetic Compounds

| Ex. | Cyclobutane | Reactants | Density $(d_t^t)$ | Boiling Point |
|---|---|---|---|---|
| VIII | 1-bromo-1,2,2-trifluoro- | $BrFC=CF_2$ + ethylene | $1.686^{24}$ | 96.5°C |
| IX | 1-bromo-2-methyl-1,4,4-trifluoro- | $BrFC=CF_2$ + propylene | $1.578^{24.5}$ | 113°C |
| X | 1-bromo-2-chloro-1,4,4-trifluoro- | $BrFC=CF_2$ + vinyl chloride | $1.813^{26}$ | 124°C |

*Cyclization followed by reduction with lithium aluminum hydride.

The anesthetic compounds shown in Table I are clear liquids at room temperature. They can be stored in containers of the type commonly used for conventional anesthetics of comparable boiling point; e.g., halothane, and they can be administered by means of apparatus or machines designed to vaporize liquid anesthetics and mix them with air, oxygen or other gaseous combinations in amounts capable of supporting respiration. It is further contemplated that the compounds herein disclosed may be used in admixture wth pharmaceutically acceptable diluents and stabilizers such as thymol, or in combination with one or more of the known inhalation anesthetics; e.g., nitrous oxide, ether, halothane chloroform, methoxyfluorane and the like. Futhermore, the compounds disclosed may be used as solvents in the manner of other halogenated hydrocarbons with the more highly substituted species being non-flammable.

ANESTHETIC PROPERTIES

The physiological effects of the compounds of this invention were demonstrated upon mice, using a standard test for evaluation of inhalation anesthetics similar to that described by Robbins [Pharmacology and Experimential Therapeutics 86, 197 (1946)]. In this test, mice were exposed to the compounds for a period of 10 minutes in a rotating drum. Observations were then made of the pinch reflex, the corneal reflex and the return of the righting reflex. At least four graded doses were employed to determine the minimum concentration required to anesthetize 50% of the mice used ($AC_{50}$) and the minimum concentration required to kill 50% of the mice ($LC_{50}$). The anesthetic index (AI) was then calculated from these minimum concentrations. The data obtained with the compounds of Examples I to XIII are presented in Table 2 along with, for comparison purposes, results obtained from similar testing of 1,2-dihydrohexafluorocyclobutane, the compound of the prior art, a closely related analog, 1,1,2,2-tetrafluorocyclobutane, and another chlorofluoro anesthetic, 1,1,2-trichloro-2,3,3-trifluorocyclobutane.

TABLE 2

| Ex | Cyclobutane | Anesthetic Data | | AI |
|---|---|---|---|---|
| | | $AC_{50}$ | $LC_{50}$ (% volume) | |
| I. | 1,4-dichloro-1,2,2-trifluoro-, b.p. 104°C | 0.2% | 0.8% | 4 |
| | 1,4-dichloro-1,2,2-trifluoro-, b.p. 107°C | 0.2% | 1.2% | 6 |
| II. | 1-chloro-1,2,2,4-tetrafluoro- | 0.5% | 3–3.5%* | 6+ |
| III. | 1,4-dichloro-1,2,2,4-tetrafluoro- | 0.43–2% | 2–3% | 1+ |
| IV. | 1-chloro-2,3,3-trifluoro- | 0.75–1% | 4+% | 4+ |
| V. | 1-chloro-1,2,2,3,3-pentafluoro- | 2% | 10% | 5 |
| VI. | 1-chloro-2,4,4-trifluoro- | < 1% | 2% | 2+ |
| VII. | 1,2,2-trifluoro- | < 4% | 8% | 2+ |
| VIII. | 1-bromo-1,2,2-trifluoro- | < 0.5% | 3.5% | 7+ |
| IX | 1-bromo-2-methyl-1,4,4-trifluoro- | 0.5–1% | 1.5–1.75% | 1.5+ |
| X. | 1-bromo-2-chloro-1,4,4-trifluoro- | < 0.2% | 0.5% | 2.5+ |
| XI. | 1,2-dihydrohexafluoro-,b.p. 63° | 1.9% | — | — |
| | 1,2-dihydrohexafluoro-,b.p. 26° | 10.5% | — | — |
| XII. | 1,1,2,2-tetrafluoro- | 4% | 12% | — |
| XIII. | 1,1,2-trichloro-2,3,3-trifluoro- | 0.2% | 1% | 5 |

*Where two percentages are given, the actual vapor concentration lies between the two values.

The results shown in Table 2 demonstrate that the compounds tested in Examples I to X are potent anesthetics with differing but generally high margins of safety, as indicated by the anesthetic index values (AI). In this respect, it would be noted that halothane, an important conventional acyclic halogenated anesthetic, has an index of about 3 when tested in the present manner. The values given for the anesthetic concentrations of the cis- and trans- isomers of 1,2-dihydrohexafluorocyclobutane in Example XI are those reported by Burns et al [Anesthesia 19 (2), 176 (1964) and 16 (1), (1961)] and reviewed in Larsen and Kranz & Rudo cited earlier.

While each of the compounds shown in the table has proved capable of inducing a state of general anesthesia in air-breathing mammals from which the animals soon recover provided that lethal concentrations of anesthetic vapors ($LC_{50}$) are not reached, it has been determined on retesting the hexafluorocyclobutanes of the art in the manner of Examples I to X,XII and XIII, that the animals used in such tests die within thity hours from the time of exposure although they at first apparently recover successfully from the state of anesthesia induced by the compounds in question. The same "delayed death" phenomenon has been observed in tests with compound XIII, a compound which otherwise would have been considered an excellent anesthetic in terms of potency and safety margin.

In contrast to these findings, all test mice used in Example I to X were still living one week after exposure.

Similarly, the tetrafluoro compound of Example XII, which might have been considered as a satisfactory, safe weak anesthetic on the basis of a quick determination of its anesthetic and lethal concentrations ($AC_{50}$, 4%; $LC_{50}$, 12; AI, 3), proved to be a convulsant on further observation. This compound, which is one of the numerous halogenated cyclobutanes that have been found deleterious, is of particular interest in that its close structural relationship to the 1,2-dihydrohexafluorocyclobutane isomers of the art and to the useful trifluoro (Ex. VII) homolog disclosed above provides a good illustration of the unpredictability in physiological behavior in the field of anesthesia.

What is claimed is:

1. The cyclobutanes selected from the group consisting of 1,4-dichloro-1,2,2-trifluorocyclobutane, 1-chloro-1,2,2,4-tetrafluorocyclobutane, 1,4-dichloro-1,2,2,4-tetrafluorocyclobutane, 1-chloro-1,2,2,3,3-pentafluorocyclobutane, 1,2,2-trifluorocyclobutane,[1-chloro-2,3,3,-trifluorocyclobutane, 1-chloro-2,4,4-trifluorocyclobutane 1-bromo-1,2,2-trifluorocyclobutane], 1-bromo-2-methyl-1,4,4-trifluorocyclobutane and 1-bromo-2-chloro-1,4,4-trifluorocyclobutane.
2. 1,4-Dichloro-1,2,2-trifluorocyclobutane.
3. 1-Chloro-1,2,2,4-tetrafluorocyclobutane.
4. 1,4-Dichloro-1,2,2,4-tetrafluorocyclobutane.
5. 1-Chloro-1,2,2,3,3-pentafluorocyclobutane.
6. 1,2,2-Trifluorocyclobutane.
7. 1-Bromo-2-methyl-1,4,4-trifluorocyclobutane.
8. 1-Bromo-2-chloro-1,4,4-trifluorocyclobutane.

* * * * *

UNITED STATES PATENT AND TRADEMARK OFFICE
CERTIFICATE OF CORRECTION

PATENT NO. : 3,954,893
DATED : May 4, 1976
INVENTOR(S) : Gerald J. O'Neill, Robert S. Holdsworth, Charles W. Simons It is certified that error appears in the above—identified patent and that said Letters Patent are hereby corrected as shown below:

Claim 1, column 6, lines 6, 7 and 8,
Delete the following text:

---[1-chloro-2,3,3-trifluorocyclobutane, 1-chloro-2,4,4-trifluorocyclobutane and 1-bromo-1,2,2-trifluorocyclobutane]---

Signed and Sealed this

Twentieth Day of July 1976

[SEAL]

*Attest:*

RUTH C. MASON
*Attesting Officer*

C. MARSHALL DANN
*Commissioner of Patents and Trademarks*